United States Patent
Sander

(10) Patent No.: US 7,057,807 B2
(45) Date of Patent: *Jun. 6, 2006

(54) MICROSCOPE

(75) Inventor: Ulrich Sander, Rebstein (CH)

(73) Assignee: Leica Microysstems (Schweiz) AG, Heerbrugg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/860,517

(22) Filed: Jun. 3, 2004

(65) Prior Publication Data

US 2005/0018281 A1    Jan. 27, 2005

(30) Foreign Application Priority Data

Jun. 5, 2003    (DE) .............................. 103 25 575

(51) Int. Cl.
*G02B 21/00* (2006.01)
*G02B 21/18* (2006.01)

(52) U.S. Cl. .................. 359/380; 359/368; 359/372; 359/431

(58) Field of Classification Search ........ 359/368–390, 359/431, 850–861; 351/200–247
See application file for complete search history.

(56) References Cited

U.S. PATENT DOCUMENTS

| | | | | |
|---|---|---|---|---|
| 4,299,439 A | * | 11/1981 | Stromblad | .................. 359/384 |
| 4,547,047 A | * | 10/1985 | Koike et al. | .................. 359/375 |
| 4,938,575 A | | 7/1990 | Kleinberg et al. | .......... 359/377 |
| 5,002,376 A | | 3/1991 | Hoppl et al. | ................. 359/377 |
| 5,052,789 A | | 10/1991 | Kleinberg | .................... 359/375 |
| 5,535,052 A | * | 7/1996 | Jorgens | ..................... 359/388 |
| 5,552,929 A | * | 9/1996 | Fukaya et al. | ............... 359/380 |
| 5,822,114 A | | 10/1998 | Hanzawa | ..................... 359/380 |
| 6,208,462 B1 | * | 3/2001 | Yonetani | ..................... 359/434 |
| 6,327,079 B1 | * | 12/2001 | Namii et al. | ................. 359/376 |
| 6,473,229 B1 | | 10/2002 | Nakamura | ................... 359/377 |
| 6,816,304 B1 | * | 11/2004 | Nakamura et al. | .......... 359/388 |
| 2001/0010592 A1 | | 8/2001 | Nakamura | .................. 359/376 |

FOREIGN PATENT DOCUMENTS

EP    1424581 A2    2/2004

* cited by examiner

*Primary Examiner*—Thong Q Nguyen
(74) *Attorney, Agent, or Firm*—Hodgson Russ LLP

(57) ABSTRACT

Microscope, particularly a stereomicroscope, for simultaneous observation of an object by a first and a second observer, comprising a main objective (2) having an optical axis (2a); an optical viewing path; a plurality of deflector elements (5, 6, 7) for deflecting the optical viewing path into a first plane I extending at an angle to the optical axis of the main objective and subsequently into a second plane II substantially parallel to and above the first plane I; an uncoupling device (7) in the optical viewing path for uncoupling an optical viewing path of the second observer from an optical viewing path of the first observer; and a deflector element (20) for deflecting the optical viewing path of the second observer into a third plane III which extends substantially parallel to the first and second planes I, II, wherein the second plane II is located between the first plane I and the third plane III.

10 Claims, 1 Drawing Sheet

MICROSCOPE

CROSS REFERENCE TO RELATED APPLICATIONS

The present application claims priority of German patent application number 103 25 575.3 filed Jun. 5, 2003, which is incorporated herein by reference.

FIELD OF THE INVENTION

The present invention relates to microscopes, particularly stereomicroscopes, for simultaneous observation of an object by a first observer and a second observer.

BACKGROUND OF THE INVENTION

New operating techniques in modern day neurosurgery require both a main operator and an assistant to view the same operating area at the same time. The main operator and assistant should be able to view the same field of vision. This requirement is difficult to meet in practice as the microscope has to be able to be oriented in all directions in space and must be capable of being operated in all these orientations.

The Japanese manufacturer Olympus has developed a microscope which can be used in neurosurgery in which the solution is essentially based on the use of a magnification system which does not give rise to any stereoscopic splitting. This makes the development of such a microscope easier on the one hand but gives rise to serious defects which are not acceptable to the users in certain fields of application. One such defect is for example the fact that the three dimensional impression varies with the magnification.

Application publication U.S. 2001/0010592 A1 discloses a stereomicroscope in which the optical channels of observation for the main operator and assistant are split in front of the respective objective and magnification systems. The optical viewing paths for the main operator, after passing through a first main objective, are deflected into the horizontal, while a corresponding magnification system for the main operator is arranged horizontally. The assistant microscope is arranged underneath the main microscope. A disadvantage of this is that the free working interval underneath the microscope (i.e. the distance between the microscope and the object which is to be observed) is reduced and the overall height of the microscope as a whole is increased. As a separate main objective is also required for the assistant microscope, this microscope also proves to be relatively complicated in the provision of the respective optical components.

SUMMARY OF THE INVENTION

The aim of the invention is to provide a microscope, particularly a stereomicroscope, for simultaneous viewing by a first and a second observer (main operator and assistant) wherein the free working space underneath the microscope is restricted as little as possible while the overall height of the microscope is kept to a minimum.

This objective is achieved by means of a microscope comprising a main objective having an optical axis; an optical viewing path; a plurality of deflector elements for deflecting the optical viewing path into a first plane I extending at an angle to the optical axis of the main objective and subsequently into a second plane II substantially parallel to and above the first plane I; an uncoupling device in the optical viewing path for uncoupling an optical viewing path of the second observer from an optical viewing path of the first observer; and a deflector element for deflecting the optical viewing path of the second observer into a third plane III which extends substantially parallel to the first and second planes I, II, wherein the second plane II is located between the first plane I and the third plane III.

According to the invention, a microscope which may be used in neurosurgery, for example, particularly a stereomicroscope, is made available wherein the free working interval underneath the microscope is maximum and is in no way restricted by the positioning of an assistant microscope. The microscope provided according to the invention also has a lower overall height compared with conventional microscopes.

The microscope according to the invention also ensures that both the main operator and an assistant are provided with a stereoscopic image impression irrespective of the magnification set, the field of viewing being substantially the same for the main operator and the assistant. It has also proved advantageous that the microscope according to the invention uses only one main objective, as the splitting of the optical paths into the main operator's optical paths and the assistant's optical paths only takes place after the optical paths have passed through the main objective.

The goals set out are essentially achieved by the fact that the optical paths undergo deflections after passing through the main objective so that a total of three substantially parallel optical path planes are produced. The uncoupling of the optical paths for the assistant or assistant microscope takes place such that this optical path extends in the uppermost of the three planes, i.e. in the plane at the greatest distance from the object which is to be observed.

According to a particularly preferred embodiment of the microscope according to the invention, a magnification system for the first observer (main operator) is arranged in the second or middle plane of the microscope and a magnification system for the second observer (assistant) is arranged in the third (uppermost) plane of the microscope. This measure of arranging the magnification systems for the first and second observers in the second and third planes extending substantially horizontally, in particular, means that the overall height of the microscope as a whole can be kept to a minimum. Because different magnification systems are provided for the first and second observers, different magnifications can be set for the first observer (main operator) and second observer (assistant) as necessary. It should be mentioned that the horizontal extent of the planes of the microscope, particularly when the microscope according to the invention is used in the field of neurosurgery, is only a preferred orientation. In theory, the microscope according to the invention should be able to be oriented so that the planes extend diagonally in space, preferably parallel to one another.

Expediently, at least one of the magnification systems for the first or second observer has a zoom lens or zoom system. With a zoom lens of this kind it is possible to achieve the desired magnification tailored to individual requirements over a given zoom range.

According to another preferred embodiment of the microscope according to the invention the optical viewing paths are pivotable in the second plane and/or the third plane. This measure means, for example, that the assistant's microscope can be freely used in all directions in space, thus effectively avoiding getting in the way of the main operator.

Conveniently, at least one of the deflecting devices by means of which the optical viewing paths can be deflected from one of the planes into another plane is semi-transparent. This allows the assistant's optical paths to be uncoupled without restricting the optical path pupils (physical beam splitting). In this way vignetting can be effectively avoided.

According to another preferred embodiment of the microscope according to the invention, the magnification systems for the first and second observer are mechanically and/or electrically coupled to one another. This ensures that, particularly when using zoom systems as the magnification system, the same magnifications can be achieved for both observers or the magnifications selected can be varied synchronously with one another.

BRIEF DESCRIPTION OF THE DRAWING

The invention is described more fully with reference to the attached drawing, wherein.

DETAILED DESCRIPTION OF THE INVENTION

Figure 1:
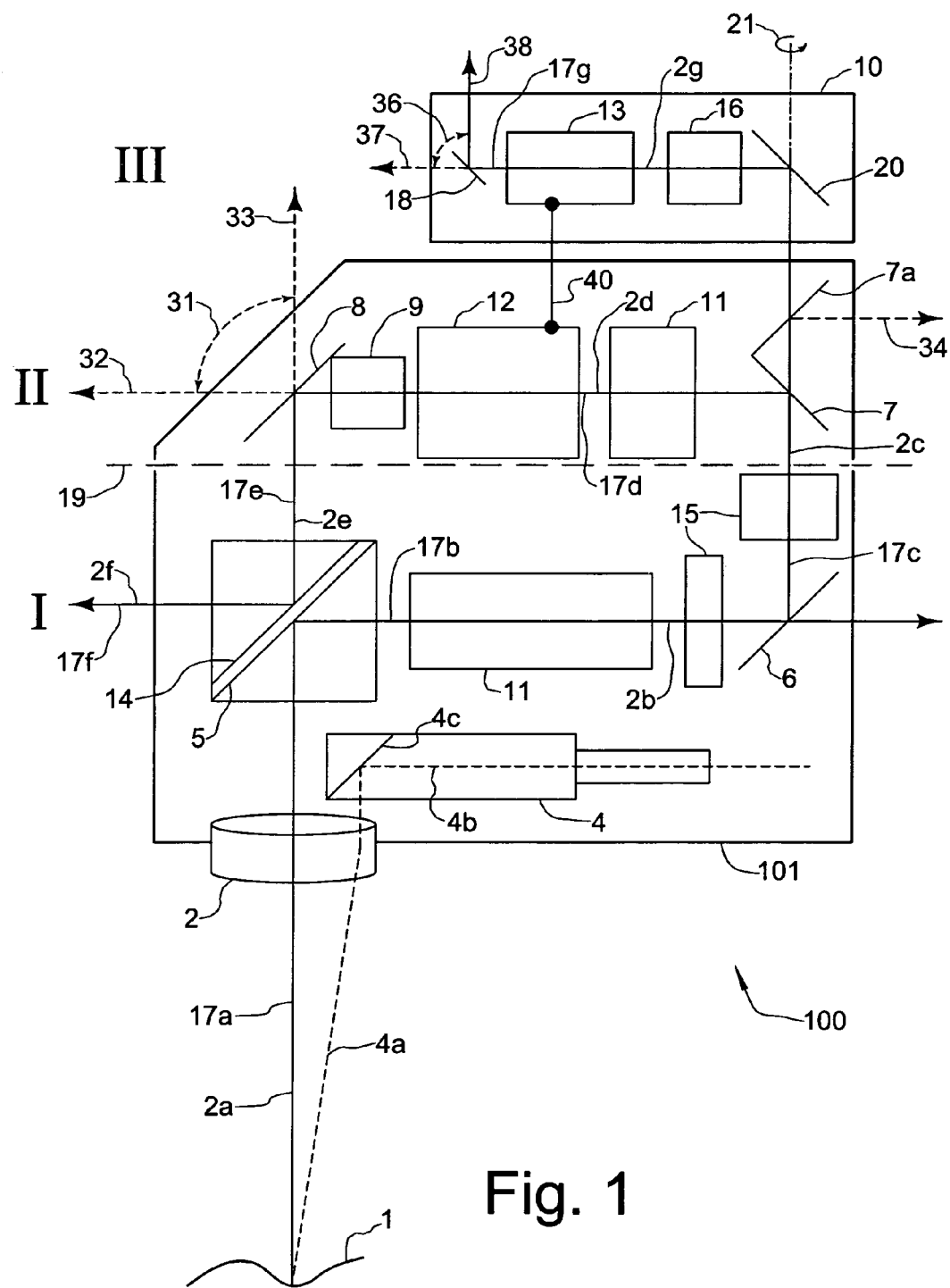
FIG. 1 shows a preferred embodiment of the microscope according to the invention in diagrammatic sectional side view.

A preferred embodiment of a microscope according to the invention in the form of a stereomicroscope is generally designated 100 in FIG. 1. The microscope 100 is intended to be used to observe, for example, a neurological object 1. An illuminating device which illuminates the object 1 along an illumination axis 4a is generally designated 4. Microscope 100 generally comprises a main microscope portion 101 and an assistant microscope portion 10.

The object 1 is imaged into the microscope 100 through a main objective 2. The optical axis of the main objective 2 is designated 2a. In the embodiment shown it runs substantially vertically, while it should be pointed out that the microscope 100 and hence the optical axis 2a as well is capable of being oriented in every direction in space. Passing through the main objective 2 is an optical viewing path 17a which runs along the optical axis 2a. The optical viewing path 17a is then deflected by a deflecting element 5 into a first plane I of the microscope. The optical axis in the first plane I is designated 2b and the deflected optical path is designated 17b. In the first plane I of the microscope are mounted optical components 11, 15 which produce intermediate images in the optical viewing path 17b, for example. The optical viewing path 17b extending in the first plane I of the microscope is then deflected by a deflecting element 6 along an axis 2c into the vertical direction and then by another deflector element 7 into a second plane II of the microscope extending substantially horizontally and parallel to the first plane I. Optical components 15 such as data projectors, shutters, filters, transparent displays, beam deflector systems or image rectifiers may be incorporated in the optical path 17b and in the vertical optical path designated 17c between the deflector elements 6 and 7. Optical components which produce intermediate images may also be included in the optical path 17c. Components of this kind have already been mentioned and designated by reference numeral 11. Such components are not explicitly shown for the vertical optical path 17c. For the sake of completeness it should be pointed out that the sequence of the components 11 and 15 as shown in the drawing is purely an example. It would be equally possible to arrange first the components 15 and then the components 11 along the optical viewing path 17b, for example. The same is obviously true of the arrangement of these components along the optical viewing paths 17c or 17d. The optical viewing path designated 17d which extends in the second plane II of the microscope initially passes through other optical components which provide intermediate images and are all collectively designated 11. As already mentioned, optical components as designated 15 hereinbefore may also be provided along the optical viewing path 17d. These components are arranged along an optical axis 2d. Adjacent to these optical components 11 the optical viewing path 17d meets a first magnification system 12 for a first observer (main operator). This magnification system 12, which is expediently constructed as a zoom system, has two observation channels and thus splits the optical viewing path 17d which has exited the optical components 11 into two stereoscopic optical paths for the first observer (main operator).

Other optical components may be incorporated behind the magnification system 12. For example, an optical splitter 9 for camera documentation is provided in the embodiment shown.

By means of another deflecting element 8 the stereoscopic optical viewing paths can be deflected down again as optical viewing paths 17e along optical axis 2e, for example into the first plane I of the microscope. Another deflector element 14 is provided here which defines optical viewing paths 17f and the direction of observation or viewing for the first observer (main operator) along an optical axis 2f. Binocular tubes adjacent to the deflector element 14 for the main observer are not shown, so as to keep the drawing simple. In order to give the main operator a physiologically favourable view (i.e. a substantially horizontal view) even when the microscope is positioned diagonally in space the deflector element 14 is expediently rotatable about an axis extending perpendicularly into the plane of the drawing, while the binocular tube (not shown) is also rotatable about the optical axis 2f.

Alternatively to viewing in the first plane I it may also be possible to do away with the deflector element 8 and thereby achieve a corresponding view for the main operator in the second plane II.

The deflector element 8 can, as mentioned, also be dispensed with, while in this case the main operator can easily view along the second plane II of the microscope. The deflector element 8 may moreover be constructed so that the first observer can view either the second plane II or the first plane I, as he wishes. In connection with this it should be pointed out that a variable viewing angle can be achieved by a suitable construction of the deflector element 8. The angular range over which this view can be pivoted is illustrated by the curved arrow 31 extending between the arrows 32 and 33. One particular embodiment of the deflector element with which pivoting of the view can be achieved, is described for example in the brochure produced by Leica entitled "Leica M 680 2×2", publication IV 2000, 10M16801de and in U.S. Pat. No. 6,172,804 B1, the disclosure of which is incorporated herein by reference. The view in the second plane II is indicated by the dotted arrow 32 which constitutes an extension of the axis 2d. A vertical view is indicated by arrow 33.

The uncoupling of the optical paths which is provided according to the invention for a second observer (assistant) is achieved using the deflector element 7 which is semi-transparent. Thus, part of the optical view path meeting the deflector element 7 is not deflected but travels further along the optical axis 2c and meets another deflector element 20 which is provided in assistant microscope portion 10. The deflector element 20, which may be semi-transparent as shown in FIG. 1, deflects the viewing beam into a third plane III of the microscope as optical viewing path 17g. Additional optical components for the assistant, generally designated 16, and a second magnification system for the assistant, designated 13, are provided in the third plane III. The optical components 16 may include, for example, an image rectifier. Optical elements already provided above with reference numerals 11 and 15 may also be incorporated here. The optical axis of the magnification system 13 is designated 2g.

The magnification system 13 for the assistant is expediently constructed in a similar manner to the magnification system 12 for the main operator, i.e. the optical viewing path 17g is divided into two stereoscopic optical viewing paths. The magnification system 13 for the assistant is also advantageously constructed as a zoom system. It is possible to construct the magnification systems 12, 13 with either different or identical magnification ranges. An electrical or mechanical coupling device 40 may be provided to ensure, for example, identical magnifications of the two magnification systems. Coupling means can be implemented for example by coupled drive units for the two zoom systems.

Adjacent to, i.e. following the magnification system 13 there are provided binocular tubes (not shown) for the assistant's view. This assistant's view is advantageously made variable by means of a rotatable deflector element 18 and for this purpose the deflector element 18 may be constructed analogously to the deflector element 8. Here again, the angular range over which the assistant's view is adjustable is indicated by a curved arrow 36 which extends analogously to the arrow 31 between the arrows 37 and 38. Moreover, the binocular tube for the assistant is constructed to rotate about the axis 2g. The assistant's microscope portion 10 is also designed to be rotatable about the axis 2c. This provides the assistant with a view which is rotatable through 360°, for example, in the third plane III of the microscope. Arrow 37 indicates a horizontal view with respect to the third plane III of the microscope, arrow 38 a vertical view.

Another, preferably semi-transparent deflector or beam splitter element 7a may be provided between the deflector elements 7 and 20, for the purpose of uncoupling optical paths, e.g. for documentation purposes (illustrated by the dotted arrow 34).

It is also possible to provide a rotatable view for the main operator. To achieve this, the part of the microscope located above the dotted line 19 simply has to be made rotatable relative to the area located below this line. This rotation can easily be achieved by rotating the deflector elements 7 and 20 about the optical axis 2c (as indicated by curved arrow 21), by virtue of the fact that stereoscopic splitting of the optical viewing paths for the main operator or assistant takes place only in the magnification systems 12 and 13.

According to the invention, all the requirements of a microscope for use in neurosurgery have been met for the first time. The assistant and main operator look through a shared main objective 2 but the assistant in no way restricts the working space. Moreover, the overall height of the microscope is not increased by the assistant or the assistant microscope portion. Nor do add-on components 9, 15, 11, 16 increase the overall height but rather allow better balancing of the microscope. Add-on components 9, 15, 11, 16 may be provided, not only at the positions shown in the drawings, but also at any other positions along the optical viewing paths 17a–17g which are not specified in detail here. Both observers have a separate magnification or zoom system with the option of conventional stereoscopic splitting (true three-dimensional impression). Moreover, the assistant microscope can be freely used in all directions in space and therefore does not interfere with the main operator. Finally it should be pointed out that the arrangement of the illuminating device 4 as shown in the drawing is provided purely by way of example. For example, it is advantageously possible to arrange the illuminating device 4 in the region of the first plane I of the microscope between the deflector elements 5 and 6, and the light emitted from the illuminating element may advantageously be deflected by the deflector element 5 onto the main objective 2 or the object 1 which is to be observed. The deflector element 5 could also replace the deflector element 4c of the illuminating device 4, in a corresponding arrangement. It would also be possible to make the main axis 4b of the illuminating device 4 perpendicular and deflect light onto the deflector element 5 by means of a suitably aligned deflector element 4c of the illuminating device 4. Using this measure, the overall height of the microscope can optionally be reduced still further.

LIST OF REFERENCE NUMERALS

1 Object
2 Main objective
2a Optical axis of the main objective
2b–2g Optical axes
4 Illuminating device
4a Illuminating axis
4b Main direction of the illuminating device
4c Deflector element of the illuminating device
5, 6, 7, 7a, 8 Deflector elements
9 Optical splitter
10 Assistant microscope portion
11 Optical components or intermediate imaging systems
12 Magnification system for main operator
13 Magnification system for assistant
14 Deflector element
15 Optical components
16 Optical components for assistant
17a–17g Optical viewing paths
18 Deflector element
19 Dotted line
20 Deflector element
21, 31, 36 Curved (rotational) arrows
32–34, 37, 38 Arrows
40 Magnification system coupling means
100 Microscope
101 Main microscope portion

What is claimed is:
1. A microscope for simultaneous observation of an object by a first and a second observer, the microscope comprising:
a main objective having an optical axis;
an optical viewing path;
a plurality of deflector elements for deflecting the optical viewing path into a first plane (I) extending at an angle to the optical axis of the main objective and subsequently into a second plane (II) substantially parallel to and above the first plane (I);
an uncoupling device in the optical viewing path for uncoupling an optical viewing path of the second observer from an optical viewing path of the first observer;
a deflector element for deflecting the optical viewing path of the second observer into a third plane (III) which extends substantially parallel to the first and second planes (I, II), the second plane (II) being located between the first plane (I) and the third plane (III); and
a magnification system in the second plane (II) for the first observer, and another magnification system in the third plane (III) for the second observer.

2. The microscope according to claim 1, wherein the first plane (I) extends substantially perpendicularly to the optical axis of the main objective.

3. The microscope according to claim 1, wherein at least one of the magnification systems comprises a zoom system.

4. The microscope according claim 1, wherein the optical viewing path of the first observer is rotatable in the second plane (II) by rotation of one of the plurality of deflector elements.

5. The microscope according claim 1, wherein the optical viewing path of the second observer is rotatable in the third plane (III) by rotation of the deflector element for deflecting the optical viewing path of the second observer into third plane (III).

6. The microscope according claim 1, wherein at least one of the plurality of deflector elements is semi-transparent.

7. The microscope according claim 1, wherein the deflector element for deflecting the optical viewing path of the second observer into third plane (III) is semi-transparent.

8. The microscope according to claim 1, wherein the optical viewing path of the first observer, after passing through the main objective, is split into two stereoscopic optical viewing paths in the magnification system in the second plane (II).

9. The microscope according to claim 1, wherein the optical viewing path of the second observer, after passing through the main objective, is split into two stereoscopic optical viewing paths in the magnification system in the third plane (III).

10. The microscope according claim 1, further comprising means for coupling the magnification system in the second plane (II) with the magnification system in the third plane (III).

* * * * *

UNITED STATES PATENT AND TRADEMARK OFFICE
CERTIFICATE OF CORRECTION

PATENT NO. : 7,057,807 B2  
APPLICATION NO. : 10/860517  
DATED : June 6, 2006  
INVENTOR(S) : Ulrich Sander Page 1 of 1

It is certified that error appears in the above-identified patent and that said Letters Patent is hereby corrected as shown below:

Title page, item (73), the assignee should read:
--Leica Microsystems (Schweiz) AG--.

Signed and Sealed this

Twenty-second Day of August, 2006

JON W. DUDAS  
*Director of the United States Patent and Trademark Office*